United States Patent [19]
Lindegren et al.

[11] Patent Number: 5,376,109
[45] Date of Patent: Dec. 27, 1994

[54] MEDICAL ELECTRODE DEVICE

[75] Inventors: Ulf Lindegren, Enskede; Per Nyman, Belestigen, both of Sweden

[73] Assignee: Siemens Aktiengesellschaft, Munich, Germany

[21] Appl. No.: 73,516

[22] Filed: Jun. 9, 1993

[30] Foreign Application Priority Data

Jun. 16, 1992 [SE] Sweden ................ 92-1846

[51] Int. Cl.⁵ ................................. A61N 1/00
[52] U.S. Cl. ......................... 607/122; 128/772
[58] Field of Search .................. 128/642, 772; 607/119–123, 125, 129

[56] References Cited

U.S. PATENT DOCUMENTS

| | | | |
|---|---|---|---|
| 3,804,098 | 4/1974 | Friedman | 607/122 |
| 3,847,140 | 11/1974 | Ayella | 128/772 |
| 4,677,990 | 7/1987 | Neubauer . | |
| 4,798,598 | 1/1989 | Bonello et al. | 128/772 |
| 4,920,980 | 5/1990 | Jackowski . | |
| 4,957,110 | 9/1990 | Vogel et al. . | |
| 5,170,787 | 12/1992 | Lindegren . | |

FOREIGN PATENT DOCUMENTS 2516848 10/1976 Germany .

*Primary Examiner*—William E. Kamm
*Assistant Examiner*—Marianne H. Parker
*Attorney, Agent, or Firm*—Hill, Steadman & Simpson

[57] ABSTRACT

An electrode device for intracorporeal stimulation of body tissue, in particular for intracardial stimulation of heart tissue, has an electrode cable containing a coiled, flexible, insulated first wire running along substantially the entire length of the electrode cable and whose interior forms a channel, with at least one partially conductive electrode head provided on the distal end of the electrode cable. The cable also contains a second wire provided in the channel, this second wire running coaxially along the entire length of the electrode cable and being attached at or near the distal end of the electrode cable. The proximal end of the second wire extends beyond the proximal end of the electrode cable, a device for displacing the second wire in relation to the electrode cable in a selected way is provided so that by compressing the coiled first wire the electrode cable can be made stiff or pliant, as desired, with the need for a stylet.

7 Claims, 1 Drawing Sheet

MEDICAL ELECTRODE DEVICE

BACKGROUND OF THE INVENTION

1. Field of the Invention

The present invention relates to an electrode device for intracorporeal stimulation of body tissue, in particular for intracardial stimulation of heart tissue of the type having an electrode cable containing a coiled, flexible, insulated first wire running substantially the entire length of the electrode cable, and whose interior forms a channel, with at least one partially conductive electrode head provided on the distal end of the electrode cable, and with a second wire provided in the channel, wire running the entire length of the electrode cable and attached at or near the electrode cable's distal end.

2. Description of the Prior Art

It is of major importance for the electrode cable in an electrode of this type to be sufficiently pliant to enable it to follow the venous pathway during introduction into a patient's heart through a vein without damaging venous walls. For conventional electrodes, the cable is introduced with the aid of a stylet, inserted into the cable's channel, made of a material offering the stiffness which is required for advancing the electrode cable through veins. The stiffness of the electrode cable can be varied, depending on the stylet's diameter and material. At awkward passages in which the electrode cable must be, e.g., bent sharply, the styler is often retracted a little to maximize the pliability of the electrode cable's distal end. (As used herein, "distal" means distal relative to a yet-to-be connected stimulation device, and the "distal end" of the electrode cable is the end which will come into contact with heart tissue. The "proximal end" of the electrode cable is the end which will be connected to the stimulation device.) After the cable has traversed such a passage, the stylet is again advanced to the distal end of the electrode cable so as to advance this end to the atrium or ventricle of the heart until the electrode head presses against heart wall for stimulation of the heart. Introduction of an electrode cable into a vein with the aid of a stylet is therefore not an entirely simple procedure for the surgeon.

An electrode device of the above-mentioned kind is disclosed in U.S. Pat. No. 4,677,990. The end of the second wire is attached to the electrode head. This wire runs the entire length of the channel and is eccentrically arranged between the first wire and the electrode cable's external insulation. When the surgeon pulls on the wire, the distal end of the electrode cable is bent into a J-shape. Introduction of the electrode cable into a patient's heart is performed with the aid of a stylet.

Another similar electrode device is prior art through the German OS 25 16 848. The function of the second wire in this electrode device is to release a spring-loaded anchor provided on the electrode head. The proximal end of the wire also runs through a lateral hole in the proximal end of the electrode cable. As a result of the wire's position inside the electrode cable, the electrode cable bends when the wire is tensioned until the distal end of the electrode cable assumes a J-shape. There is no description in German OS 25 16 848 of the way in which the electrode cable is introduced into the patient's heart.

SUMMARY OF THE INVENTION

It is an object of the present invention to provide an electrode device of the above-described type with an electrode cable which, using simple means without the aid of stylet, can be changed from being extremely pliant and flexible to being stiff, as desired.

This problem is solved in accordance with the principles of the present invention in an electrode device having a first, coiled conductor wire and having a second wire running coaxially the entire length of the electrode cable, the second wire's proximal end extending beyond the electrode cable's proximal end. The electrode device includes means for displacing the second wire in relation to the electrode cable in a defined way. Tensioning the second wire with the aid of the displacing means at the same time as the electrode cable's proximal end is held stationary causes the first coiled wire to be longitudinally compressed. Depending on the extent of the tensioning, the electrode cable becomes stiffer or more pliant. In this way, the elasticity of electrode cable can be changed from stiffness to exceptional pliancy during introduction. Thus no stiff stylet is needed as an aid in the introduction of the electrode cable.

In a preferred embodiment of the invention, the second wire is a conductor connected to the electrode head. This conductor can replace the second, usually coiled conductor connected to the electrode head in known electrode cables, thereby resulting in a simpler structure for the electrode device.

In a further embodiment of the invention, the coiled first wire can terminate short of the distal end of the electrode cable, and be connected, for example, to a ring electrode spaced from the electrode head, to which the second wire is mechanically and electrically connected. As a result, the end of this electrode cable can remain pliant even when the remaining of the electrode cable is stiffened, a feature which can be an advantage especially in the passage of a sharp bend in a vein.

In another embodiment, the means for controlling the tension of the second wire includes two holders which can slide against one another, the first holder intended for attachment at the proximal end of the electrode cable and the second holder intended for attachment to the proximal end of the second wire. With these holders, defined displacement of the second wire in relation to the electrode cable can be achieved.

In an additional embodiment of the invention, the two holders form a mutually slidable part, the second holder being provided with a screw having one end pressing against the free end side of the first holder, the second holder being slidable on the first holder with the aid of the screw so that turning the screw in one direction tensions the second wire and turning the screw in the other direction relaxes the second wire. An additional refinement of the displacement of wire and electrode cable can be achieved in this way. This construction also makes it possible for the surgeon to quickly change to different degrees of electrode cable stiffness in the course of cable introduction.

DESCRIPTION OF THE PREFERRED EMBODIMENTS

Figure 1:
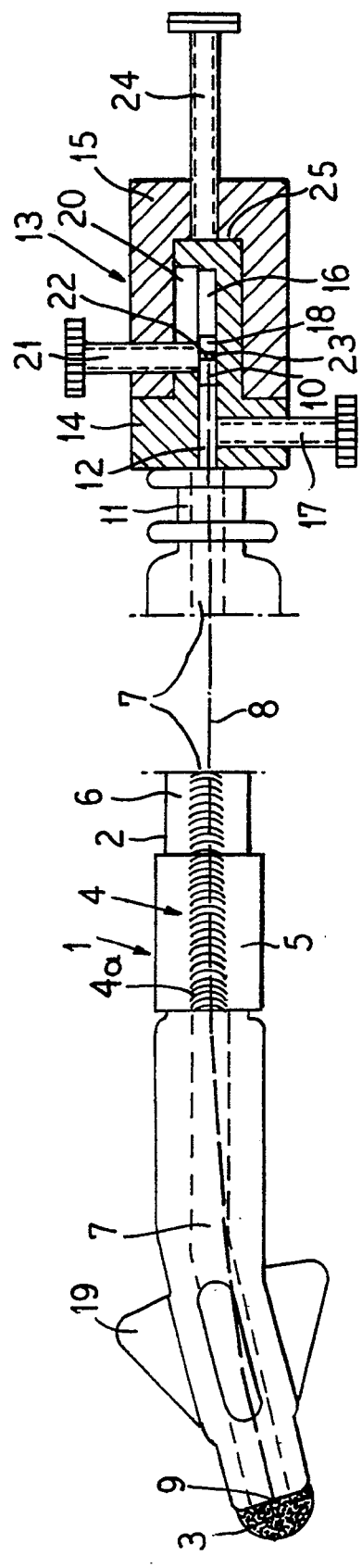
FIG. 1 shows an electrode device according to the invention with an electrode cable and a device, shown in cross-section, which tensions or relaxes a wire running inside the electrode cable, the wire in this figure being shown in a relaxed state.

FIG. 1 illustrates an electrode device 1 for intracardial stimulation of a heart. The electrode device 1, which is bipolar in this example, consists of an electrode cable 2 having a distal end at which an electrode head 3 is provided for in vivo stimulating heart tissue of a patient. The electrode cable 2 contains a coiled, flexible conductor 4 running from the proximal end 11 of the electrode cable 2 to an electrode ring 5 provided on the electrode cable 2 near the electrode head 3. The conductor 4 has coil flights 4a. The exterior of the coiled conductor 4 is covered by a layer of insulation 6, and its interior forms a channel 7. In this embodiment, continuation of the a channel 7 is provided in the material between the electrode ring 5 and the electrode head 3. Immediately behind the electrode head 3, elements 19 are provided for fixing the electrode head in the heart. A conductive wire or wires 8 runs in the channel 9 and has one end 9 attached to the electrode head 3 and an opposite end 10 extending beyond the proximal end 11 of the electrode cable 2. The wire 8, which runs coaxially the entire length of the electrode cable 2, is for carrying a voltage to the electrode head 3 from a heart stimulation apparatus (not shown) for stimulating heart tissue. The distal end of the electrode cable 2 can, as FIG. 1 shows, be advantageously curved somewhat.

The proximal end 11 of the electrode cable 2 has a pin 12 intended for connection to the heart stimulator when the electrode device has been applied in the patient's heart. A device 13 is provided at the pin 12 which contains two mutually slidable holders 14 and 15. The holder 14 has a coaxially arranged hole 16 running virtually the entire length of the holder 14. With the aid of the hole 16, the holder 14 slides on the pin 12, the holder 14 being attachable to the pin 12 with a screw 17. A sliding sleeve 18, in which the proximal end 10 of the wire 8 is permanently attached, is also provided in the hole 16. The sleeve 18 is preferably a separate part of the pin 12. The holder 14 also has a slot 20 which coincides with, and is parallel to the hole 16. The second holder 15, which is slidably arranged on the holder 14, is equipped with a screw 21 which is connected to the sleeve 18 through the slot 20. Since the sleeve 18 must not press against the wall of the hole 16, one end of the screw 21 is provided with a stud 22 which rides in a track 23 in the shell 18. The holder 15 is also equipped with a set screw 24, one end of which presses against the free end side 25 of the holder 14.

Figure 2:
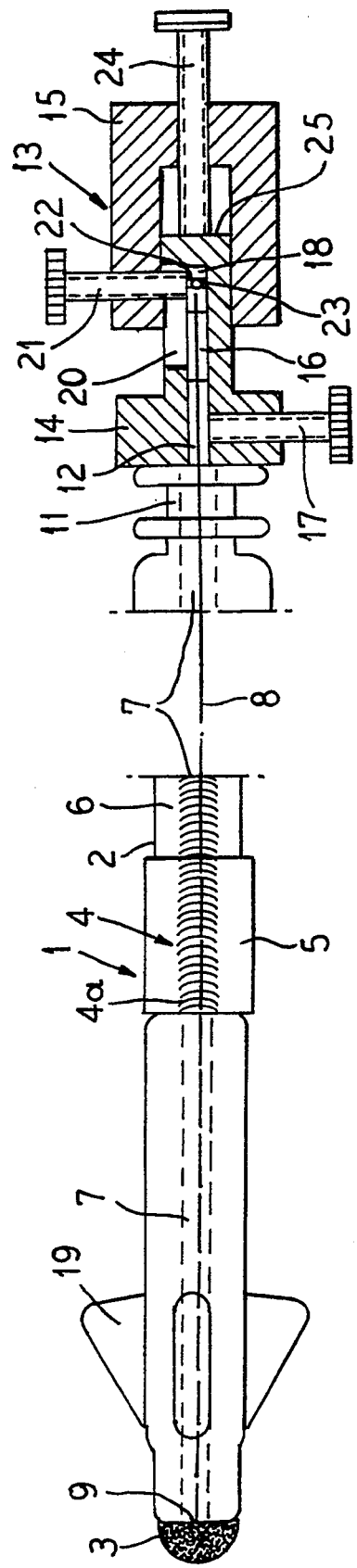
FIG. 2 shows an electrode device with an electrode cable and a device according to FIG. 1 in which the wire is shown in a tensioned state.

When the holders 14 and 15 have been slid together as shown in FIG. 1, the sleeve 18 also presses against the end side of the pin 12, the wire 8 then being slack. When the set screw 24 is turned in one direction, the holder 15 shifts in relation to the holder 14, with the screw 21 being displaced in the slot 20 and simultaneously moving the shell 18 in the hole 16. In this way, the wire 8 is displaced in relation to the electrode cable in such a way that the coiled conductor 4 is compressed by causing the flights 4a to move closer together, affecting the stiffness of the electrode cable 2. FIG. 2 shows the holder 15 in its most extended position in which the wire 8 is tensioned to a maximum. In this state, the wire 8 has also straightened the distal end of the electrode cable 2. The set screw is preferably provided with a large thread pitch so the surgeon can obtain a noticeable change in the stiffness of the electrode cable 2 with only slight rotation of the set screw 24. With the aid of the set screw 24, which controls the tension of the wire 8, the electrode cable 2 can be changed from being very pliant to being stiff during introduction into a vein. When the electrode cable 2 is in place in the heart or in a vein, the device 13 is detached from the electrode cable 2 with the screws 17 and 21 and connected to the heart stimulation device. In another embodiment of the device 13, the screws 17 and 21 can be replaced with some other kind of locking fixture.

An electrode cable 2 with a pre-curved distal end can simplify the passage of a bend in a vein. Even a severe bend in a vein can be traversed without difficulty if the electrode cable 2 is rotated around its longitudinal axis and/or the distal end is straightened out with the aid of the wire 8.

The electrode advice according to the invention can alternatively be unipolar. In such an electrode device, the coiled conductor 4 can be a coiled wire which has only a mechanical support function and which is compressed, as previously described, when the wire 8 is tensioned so the electrode cable 2 stiffens.

In another unipolar embodiment, the coiled conductor 4 can be connected to the electrode head 3 (the ring electrode 5 being omitted). In this instance, the wire 8 can be replaced with a non-conductive wire.

In another example of an electrode device according to the invention, the electrode ring 5 can be disposed on the electrode cable 2 at a more distant position from the electrode head 3 than is shown in FIGS. 1 and 2. The remainder of the electrode cable 2 between the electrode ring 5 and the electrode head 3, which is not equipped with a coiled conductor 4, can be equipped with a coiled, non-conductive wire.

Although modifications and changes may be suggested by those skilled in the art, it is the intention of the inventors to embody within the patent warranted hereon all changes and modifications as reasonably and properly come within the scope of their contribution to the art.

We claim as our invention:

1. An electrode device for intracorporeal stimulation of body tissue consisting of:

an electrode cable containing a coiled, flexible, first wire, covered by electrical insulation and extending longitudinally co-extensive with said electrode cable, said coiled, flexible first wire forming a channel inside said electrode cable, said first wire and said electrode cable each having a distal end and a proximal end, said first wire having a plurality of longitudinally compressible flights imparting a flexibility to said electrode cable;

a conductive electrode head disposed at said distal end of said electrode cable;

a second wire disposed in said channel and extending coaxially longitudinally co-extensive with said cable and mechanically attached to said distal end of said electrode cable, said second wire having a proximal end;

said first and second wires forming a wire pair and one wire in said wire pair being electrically connected to said electrode head; and means engageable with said proximal ends of said electrode cable, said first wire and said second wire for longitudinally selectively displacing said second wire relative to said electrode cable for selectively longitudinally compressing said flights of said coiled first wire for adjusting the flexibility of said electrode cable.

2. An electrode device as claimed in claim 1 wherein said second wire consists of electrically conductive material and is electrically connected to said electrode head.

3. An electrode device as claimed in claim 1 wherein said first wire terminates short of said distal end of said electrode cable so that said distal end of said electrode cable contains only said second wire.

4. An electrode device as claimed in claim 1 wherein said first wire consists of electrically conductive material, and wherein said electrode device further comprises an exposed electrically conductive surface disposed on said electrode cable spaced from said electrode head and electrically connected to said first wire.

5. An electrode device as claimed in claim 1 wherein said first wire consists of electrically conductive material and is electrically connected to said electrode head.

6. An electrode device as claimed in claim 1 wherein said means for displacing said second wire comprises first and second holders; means for mounting said first and second holders for permitting said first and second holders to slide against each other, said first holder including means for releasably attaching said first holder at said proximal end of said electrode cable and said second holder including means for releasably attaching said second holder to said proximal end of said second wire.

7. An electrode device as claimed in claim 6 wherein said first and second holders are mounted with said first holder having a side facing said second holder, said second holder having a screw with a free end pressing against said side of said first holder facing said second holder, with said second holder being slidable on said first holder, and said means for mounting including a further screw rotatable in said second holder and pressing against said first holder so that turning said further screw in a first direction applies tension to said second wire and turning said further screw in a second, opposite direction relaxes said second wire.

* * * * *